US00PP18467P2

(12) United States Plant Patent

Hardison et al.

(10) Patent No.: US PP18,467 P2

(45) Date of Patent: Jan. 29, 2008

(54) HYBRID VARIETY OF TEXAS X KENTUCKY BLUEGRASS DESIGNATED 'HB 129'

(50) Latin Name: *Texas bluegrass×Kentucky bluegrass*
Varietal Denomination: HB 129

(75) Inventors: John R. Hardison, Corvallis, OR (US); Jay B. Burr, Salem, OR (US); James R. Frelich, Salem, OR (US); George Marquez, Albany, OR (US)

(73) Assignee: OMS Investments, Inc., Los Angeles, CA (US)

( * ) Notice: Subject to any disclaimer, the term of this patent is extended or adjusted under 35 U.S.C. 154(b) by 155 days.

(21) Appl. No.: 11/197,945

(22) Filed: Aug. 5, 2005

Related U.S. Application Data

(60) Provisional application No. 60/599,539, filed on Aug. 6, 2004.

(51) Int. Cl.
*A01H 5/00* (2006.01)

(52) U.S. Cl. ..... Plt./393

(58) Field of Classification Search ..... Plt./393, Plt./388

See application file for complete search history.

(56) References Cited

U.S. PATENT DOCUMENTS

| | | | |
|---|---|---|---|
| PP3,156 | P | 7/1970 | Fuchigami et al. |
| PP3,150 | P | 5/1972 | Pepin et al. |
| PP3,186 | P | 5/1972 | Barenbrug et al. |
| PP4,336 | P | 11/1978 | Mayer et al. |
| PP6,280 | P | 9/1988 | Meier et al. |
| PP6,537 | P | 1/1989 | Meier et al. |
| PP6,538 | P | 1/1989 | Meier et al. |
| PP6,585 | P | 2/1989 | Meier et al. |
| PP7,831 | P | 3/1992 | Meier et al. |
| PP8,490 | P | 12/1993 | Meier et al. |
| PP9,036 | P | 1/1995 | Meier et al. |
| PP9,209 | P | 7/1995 | Meier et al. |
| PP9,611 | P | 7/1996 | Meier |
| PP9,848 | P | 4/1997 | Meier et al. |
| PP9,977 | P | 7/1997 | Meier et al. |
| PP10,080 | P | 10/1997 | Meier et al. |
| PP10,081 | P | 10/1997 | Meier et al. |
| PP10,384 | P | 5/1998 | Meier et al. |
| PP10,925 | P | 5/1999 | Meier et al. |
| PP11,520 | P | 9/2000 | Meier et al. |
| PP11,536 | P | 10/2000 | Meier et al. |
| PP12,435 | P2 | 3/2002 | Meier et al. |

OTHER PUBLICATIONS

Drought resistance of two texas Bluegrass hybrids compared with kentucky Bluegrass and Tall Fescue. Bremer d. et al. K–State Turfgrass Research. Report of Progress 911. 2003. p.67–44.*

Agronomy J., 41(8):393–394; Aug. 1949.

Beard et al., Beard's Turfgrass Encyclopedia for Golf Courses Grounds Lawns Sports Fields, *definitions of apomixis*, p. 23; 2005.

Bulletin of the Agricultural Experiment Station of the University of Tennessee, The Grasses of Tennessee—Part I, V(2):29, 45, 60–63, 94–97; Apr. 1892.

Curley et al., RAPD–Based Genetic Relationships in Kentucky Bluegrass: Comparison of Cultivars, Interspecific Hybrids, and Plant Inroductions, *reproduced from* Crop Sci. 44:1299–1306; 2004.

Lamson–Scibner, American Grasses –II (Illustrated), U.S. Dept. of Agriculture, Bulletin No. 17:246;1899.

Manual for Testing Agricultural and Vegetable Seeds, Agriculture Handbook, No. 30: 67–70, 224–227; 396–397, Plates VIII–X; 1952.

Piper, Blue Grasses, Meadow–Grasses and Redtop in Forage Plants and Their Culture, pp. 155–171; 1919.

Porceddu et al., Linkage mapping in apomictic and sexual Kentucy bluegrass ( Poa pratensis L.) genotypes using a two way pseudo–testcross strategy based on AFLP and SAMPL markers, Theor Appl Genet, 2002 Feb;104(2–3):273–280.

Read et al., Registration of 'Reveille' Hybrid Bluegrass, Crop Science, 39:590; Mar.–Apr. 1999.

Read et al., Texas Bluegrass (Poa arachnifera Torr.) in Turfgrass Biology, Genetics, and Breeding, Casler and Duncan, eds., pp. 61–66; 2003.

Silveus et al., Texas Grasses, Classification and Description of Grass, Descriptive Systematic Agrostology, Introduction–Illustrations XV–XVII, pp. 33–48; 1933.

Yearbook of Agriculture, U.S. Dept. of Agriculture, 75th Congress, 1st Session, House Document No. 28:1056–1070; 1937.

Yearbook of the U.S. Dept. of Agriculture, pp. 139, 145–146, Plates IV–V; 1908.

* cited by examiner

*Primary Examiner*—Kent Bell
*Assistant Examiner*—Annette H Para

(57) ABSTRACT

A hybrid variety of Texas bluegrass×Kentucky bluegrass as described, characterized by rapid establishment; a light green, dense turf; a wide leaf blade; aggressive rhizome growth; a reduced level of cotton on the seed; and a medium to high seed yield potential.

3 Drawing Sheets

BACKGROUND OF THE INVENTION

Field of the Invention

The present invention relates to a new and distinct hybrid variety of Poa arachnifera Torr.×Poa pratensis L. that has been designated as 'HB 129' bluegrass.

Description of Related Art

A Poa arachnifera×Poa pratensis hybrid designated 'Reveille' has been disclosed in PVP Certificate No. 9800337.

SUMMARY OF THE VARIETY

'HB 129' bluegrass is the result of a plant selected from the progeny of Texas bluegrass (Poa arachnifera Torr.) female plant 10–10 (seed parent), with cv. 'Geronimo' Kentucky bluegrass (pollen parent)(Poa pratensis L.) cross for perfect flowers, apomixis and turfgrass performance characteristics in the $F_1$ generation.

Texas bluegrass female plant 10—10 is an unpatented, unreleased plant selected and maintained for its tiller density, turf quality and the lack of male reproductive organs. The cv. 'Geronimo' is an unpatented, released Kentucky bluegrass of European origin from Mommersteeg International, Vlijmen, the Netherlands.

As a result of this breeding, a distinct variety was produced and asexually propagated by rhizomes, tillers and disseminules. The highly apomictic seed of 'HB 129' bluegrass was produced first at Gervais, Oreg. This seed was used to plant turf performance evaluation trials and later, seed production fields.

The seed of 'HB 129' has been found to be stable. Asexual production of 'HB 129' initially was performed at Gervais, Oreg. by propagules (tillers and rhizomes) and by disseminules (modified caryopses produced by apomixis), and has consistently produced progeny plants indistinguishable from the first generation asexual reproductions of the instant plant. The apomixis level of 'HB129' is approximately 95.0%. The apomixis level was determined by examining field planting of 'HB 129' in two years of rating for apomictic origin and from disseminules harvested over four growing seasons from field grown plants in Oregon.

'HB 129' has a number of highly desirable characteristics, including a high level of seedling vigor and rapid stand establishment; high sod strength; and provides a relatively high level of competition with Poa annua in the seedling year when compared to Kentucky bluegrass varieties. 'HB 129' has an upright leafy turf type, and a light green color which can be maintained throughout the entire growing season. 'HB 129' demonstrates good fall color and good winter color under mild winter conditions.

'HB 129' is an overall good turfgrass performer under reduced management conditions evidenced by good scores for quality under these conditions. 'HB 129' has little or no cotton (webbing) on the caryopsis. 'HB 129' has a medium to high seed yield potential in the Kentucky bluegrass seed production region of the northwestern United States and has shown the potential for economic seed production not seen in other Poa arachnifera×Poa pratensis hybrids.

In comparison with the Reveille hybrid, 'HB 129' has demonstrated relatively rapid germination and emergence in both fall and spring sowings. 'HB 129' has shown greatly reduced seed cotton as compared with 'Reveille'. It is believed that the presence of the cotton on the Reveille seed results in poor seed recovery of the hybrid and causes 'Reveille' to be available predominantly as a vegetatively reproduced product from rhizome and tiller materials.

Texas bluegrass is a vigorous sod-forming perennial native in the Southeastern and Southern Plains States. Plants grow up to 3 feet on strong soil, with numerous leaves 6 to 12 inches long and 0.025 inch wide. The grass grows throughout the winter producing abundant, nutritious pasture which is highly palatable. This is a valuable species where native, but seeding is difficult. The species is dioecious, with male and female plants. It produces only limited quantities of seed which is covered with woolly hairs that are difficult to remove. Consequently, establishment of stands for agricultural use is limited. Accordingly, Texas bluegrass exhibits similar problems to those encountered with Reveille which are overcome by the present 'HB 129' hybrid.

In comparison with a number of Kentucky bluegrass varieties 'HB 129' has an average to above-average seed size with a lower number of seeds per pound. The width of vegetative leaves of unmowed mature plants of 'HB 129' are of medium to wide, with longer ligules and with more hairs on the upper margin of the ligule, fewer hairs on the collar margin and dorsal side of the leaf sheath than Kentucky bluegrasses. The culm is longer with a relatively long panicle when compared to Kentucky bluegrass varieties. Anther color is 100% purple distinguishing 'HB 129' from most Kentucky bluegrasses.

DETAILED DESCRIPTION OF THE VARIETY

Figure 1:
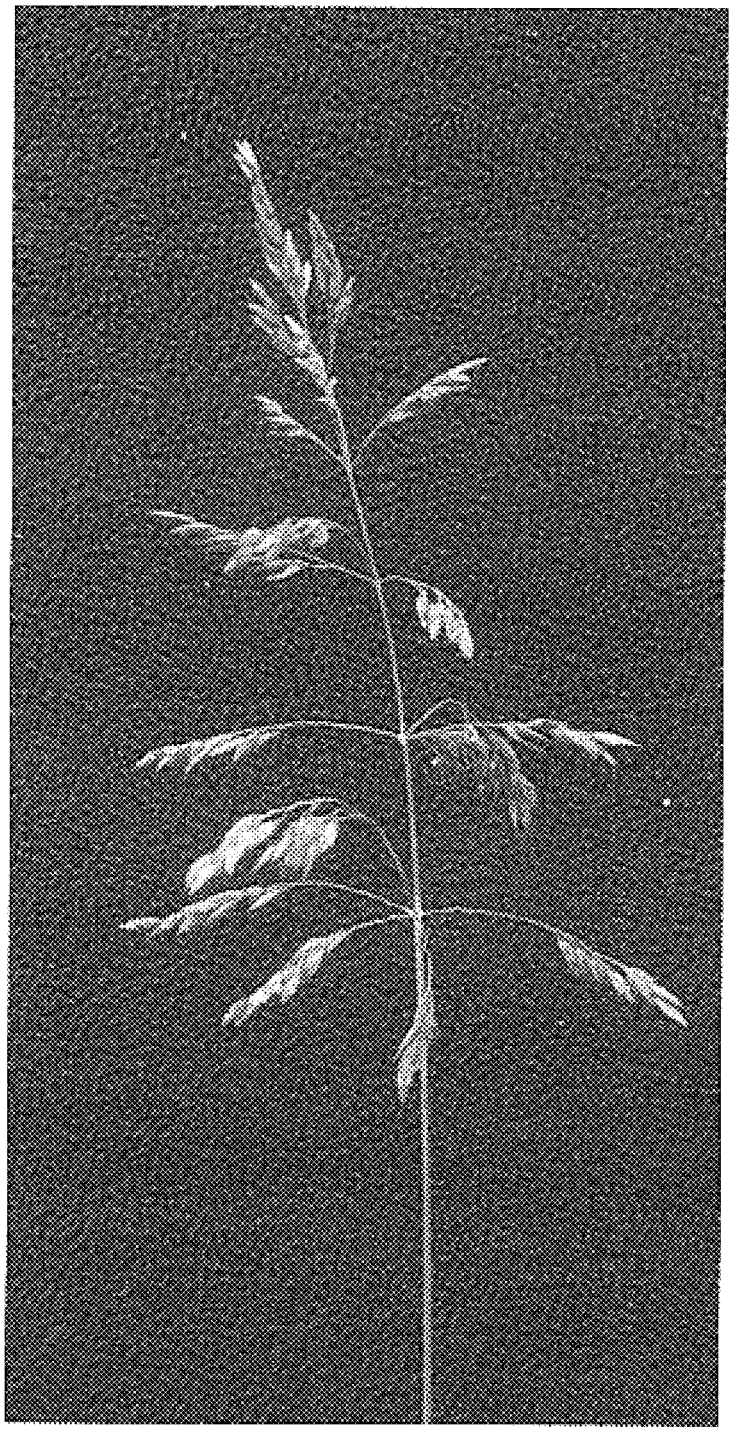
FIG. 1 is an 'HB 129' panicle.
Figure 2:
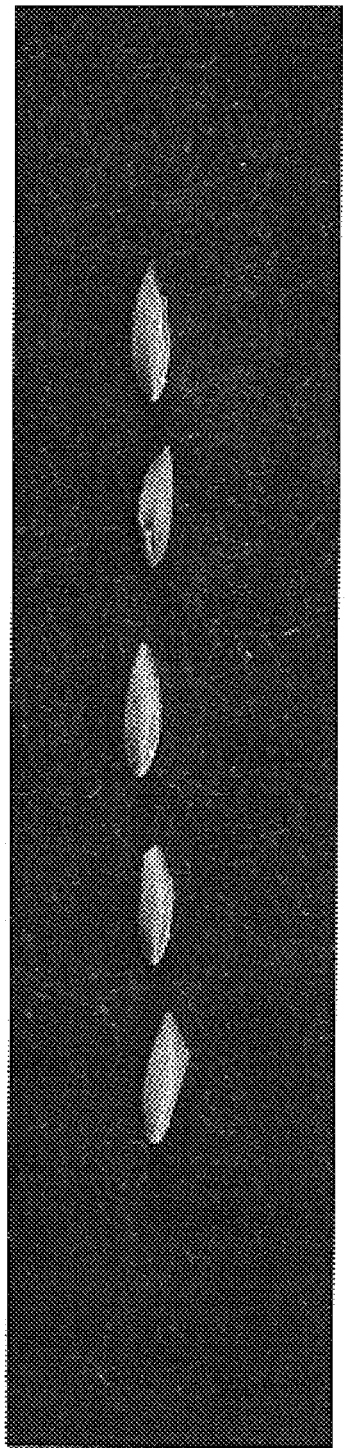
FIG. 2 is an 'HB 129' seed.
Figure 3:
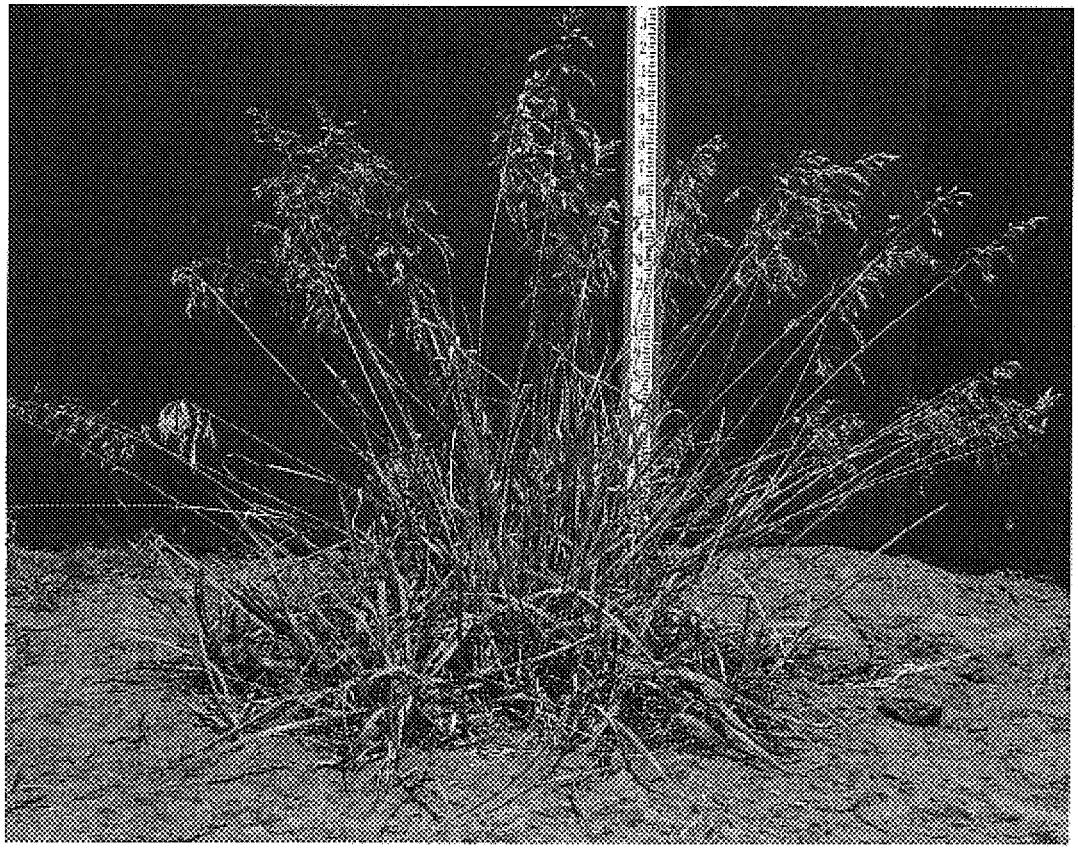
FIG. 3 is an 'HB 129' plant shortly after completing anthesis.

'HB 129' Texas bluegrass×Kentucky bluegrass (Poa arachnifera L.×Poa pratensis L.) hybrid is perennial with creeping rhizomes forming a dense turf. When plants overwinter in the field and grow undisturbed by clipping, culms are semi-erect averaging 64.8 cm in length. The vegetative leaf averages 4.5 mm in width. The flag leaf averages 6.65 cm in length, 3.55 mm in width, has a sheath length of 14.3 cm. The flag leaf averages more hairs on the ligule than other varieties. The panicle averages 10.8 cm in length. The lowest whorl of the panicle averages 4.4 branches.

For the vegetative leaf, the number of hairs is average for the leaf sheath margin, above average for the dorsal side of the leaf blade, above average for the upper margin of the ligule, and below average for the collar margin compared to other varieties. 'HB 129' differs from the Kentucky bluegrass varieties in regard to such morphological characteristics as seed length and width, culm length, and hairs on the collar margins of the vegetative leaf, on the upper surface of the vegetative leaf, on the ligule of the flag leaf and anther color.

'HB 129' produces inflorescences relatively early compared with Kentucky bluegrasses.

Since environmental conditions such as soil and climate may influence morphological characteristics to some extent, comparisons of 'HB 129' were made with Kentucky bluegrass varieties under like conditions and the comparisons are set forth in Tables 1–10, as follows.

TABLE 1

Comparison of heading date, seed yield, and plant height of 'HB 129' and other Kentucky bluegrass varieties for years 1 & 2.

| | Heading Date | | Seed Yield | | Plant Height | |
|---|---|---|---|---|---|---|
| Variety | Year 1 (Julian) | Year 2 (Julian) | Year 1 (g/10 ft row) | Year 2 (g/10 ft row) | Year 1 (cm) | Year 2 (cm) |
| 'HB 129' | 114.4 | 108.6 | 47.3 | 27.1 | 64.2 | 65.4 |
| Midnight | 126.3 | 136.3 | 33.4 | 12.0 | 54.2 | 45.5 |
| America | 125.3 | 122.8 | 29.2 | 20.4 | 40.1 | 43.3 |
| Ram I | 120.0 | 120.9 | 22.5 | 25.5 | 47.2 | 48.8 |
| Julia | 111.8 | 118.3 | 36.6 | 20.8 | 63.6 | 60.8 |
| Baron | 118.1 | 116.0 | 58.4 | 36.9 | 51.8 | 52.7 |
| Adelphia | 126.3 | 115.9 | 10.2 | 17.9 | 53.8 | 59.2 |
| Nugget | 121.1 | 114.5 | 4.7 | 4.3 | 34.3 | 30.1 |
| Langara | 118.1 | 114.3 | 31.9 | 34.8 | 46.2 | 56.0 |
| Touchdown | 105.4 | 107.3 | 55.9 | 13.0 | 57.6 | 58.7 |
| LSD (0.05) | 3.0 | 4.66 | 0.6 | 17.03 | 5.7 | 5.633 |

TABLE 2

Comparison of flag leaf position, length and width and flag leaf sheath length of 'HB 129' and other Kentucky bluegrass varieties for years 1 & 2.

| Variety | Position Year 1 | Length (mm) Year 1 | Length (mm) Year | Width (mm) Year 1 | Width (mm) Year 2 | Sheath Length (cm) Year 1 | Sheath Length (cm) Year 2 |
|---|---|---|---|---|---|---|---|
| 'HB 129' | 1.4 | 60 | 73 | 3.8 | 3.3 | 13.2 | 15.4 |
| Moon-shadow | 2.2 | 50 | 108 | 2.5 | 3.5 | 9.6 | 11.6 |
| America | 2.0 | 59 | 75 | 2.6 | 3.0 | 10.0 | 11.6 |
| Baron | 2.0 | 63 | 69 | 4.0 | 3.5 | 11.1 | 13.4 |
| Langara | 2.0 | 57 | 81 | 3.0 | 3.0 | 10.5 | 14.1 |
| Midnight | 2.0 | 74 | 86 | 3.4 | 3.2 | 10.7 | 11.4 |
| Touchdown | 1.6 | 60 | 81 | 3.5 | 3.6 | 12.9 | 16.4 |
| Adelphia | 1.5 | 53 | 79 | 3.3 | 3.2 | 10.7 | 13.4 |
| Ram I | 1.5 | 42 | 58 | 3.0 | 2.7 | 10.5 | 12.3 |
| Julia | 1.5 | 71 | 84 | 3.1 | 3.0 | 11.7 | 14.1 |
| Nugget | 1.4 | 29 | 41 | 2.2 | 2.1 | 7.4 | 9.0 |
| LSD (0.05) | 0.31 | 12.2 | 9.9 | 0.56 | 0.99 | 1.32 | 1.16 |
| | 1 = Appressed | | | | | | |
| | 2 = Open Angle | | | | | | |

TABLE 3

Comparison of panicle color, habit, branch attitude, branches in lowest whorl, length and collar height for 'HB 129' and other Kentucky bluegrass varieties, year #1.

| | Panicle Characteristics | | |
|---|---|---|---|
| Variety | Color | Habit | Branch Attitude |
| 'HB 129' | 2.0 | 1.9 | 2.9 |
| Touchdown | 2.0 | 1.9 | 2.4 |
| Baron | 1.9 | 1.9 | 2.7 |
| Midnight | 1.9 | 1.0 | 1.7 |
| Nugget | 1.8 | 1.8 | 3.0 |
| Ram I | 1.6 | 2.0 | 3.0 |
| Adelphia | 1.4 | 2.0 | 1.4 |
| Langara | 1.3 | 1.0 | 2.7 |
| Julia | 1.3 | 1.0 | 1.0 |
| Moonshadow | 1.2 | 1.1 | 2.1 |
| America | 1.1 | 2.0 | 2.4 |
| LSD (0.05) | 0.23 | 0.24 | 0.24 |
| | 1 - not red | 1 - nodding | 1 - drooping |
| | 2 - red | 2 - upright | 2 - horizontal |
| | | | 3 - ascending |

| | Panicle Characteristics | | |
|---|---|---|---|
| Variety | Number of Branches in Lowest Whorl | Length (cm) | Collar Height |
| 'HB 129' | 4.40 | 10.6 | 1.0 |
| Touchdown | 3.82 | 10.4 | — |
| Baron | 4.72 | 10.6 | 1.0 |
| Midnight | 4.58 | 10.6 | 1.0 |
| Nugget | 2.80 | 6.3 | 1.1 |
| Ram I | 3.73 | 7.7 | 1.0 |
| Adelphia | 4.01 | 10.2 | 1.1 |
| Langara | 3.78 | 9.7 | 1.0 |
| Julia | 4.52 | 11.4 | 1.0 |
| Moonshadow | 4.49 | 9.4 | 1.0 |
| America | 4.07 | 8.8 | 1.0 |
| LSD (0.05) | 0.52 | 1.07 | 0.05 |
| | | | 1 - open |
| | | | 2 - closed |

TABLE 4

Comparison of panicle color, habit, branch attitude, branches in lowest whorl, length, and collar height for 'HB 129' and other Kentucky bluegrass varieties, year 2.

| Variety | Color | Habit | Branch Attitude |
|---|---|---|---|
| 'HB 129' | 2.0 | 1.1 | 1.0 |
| Baron | 2.0 | 1.7 | 1.1 |
| Touchdown | 2.0 | 1.0 | 1.2 |
| Nugget | 1.9 | 1.0 | 1.5 |
| Midnight | 1.8 | 1.9 | 1.2 |
| Julia | 1.2 | 1.3 | 1.1 |
| Langara | 1.1 | 1.0 | 1.0 |
| Adelphia | 1.1 | 1.1 | 1.3 |
| Moonshadow | 1.0 | 1.1 | 1.0 |
| America | 1.0 | 2.0 | 1.0 |
| Ram I | 1.0 | 1.6 | 1.0 |
| LSD (0.05) | 0.2993 | 0.2553 | 0.3610 |
| | 1 = not red | 1 = nodding | 1 = drooping |
| | 2 = red | 2 = upright | 2 = horizontal |
| | | | 3 = ascending |

| Variety | Number of Branches in Lowest Whorl | Panicle Length (cm) | Collar Height |
|---|---|---|---|
| 'HB 129' | 4.4 | 11.0 | 1.0 |
| Baron | 4.8 | 10.2 | 1.1 |
| Touchdown | 3.9 | 12.5 | 1.0 |
| Nugget | 3.2 | 7.0 | 1.0 |
| Midnight | 4.4 | 9.9 | 1.8 |
| Julia | 4.2 | 11.4 | 1.2 |
| Langara | 4.3 | 12.6 | 1.2 |
| Adelphia | 4.2 | 12.3 | 1.6 |
| Moonshadow | 4.3 | 9.8 | 1.3 |
| America | 4.0 | 9.7 | 1.9 |
| Ram I | 4.3 | 8.5 | 1.0 |
| LSD (0.05) | 0.3899 | 1.578 | 0.3610 |
| | | | 1 = open |
| | | | 2 = closed |

TABLE 5

Comparison of panicle shape of rachis for 'HB 129' and other Kentucky bluegrass varieties for years 1 & 2.

| | Panicle Shape | |
|---|---|---|
| Variety | Year 1 | Year 2 |
| 'HB 129' | 1.8 | 1.9 |
| Nugget | 2.0 | 1.3 |
| Adelphia | 1.9 | 1.7 |
| Ram I | 1.9 | 1.8 |
| Moonshadow | 1.4 | 1.9 |
| Baron | 1.2 | 1.9 |
| America | 1.2 | 1.7 |
| Langara | 1.1 | 1.8 |
| Touchdown | 1.1 | 1.5 |
| Midnight | 1.1 | 1.7 |
| Julia | 1.0 | 2.0 |
| LSD (0.05) | 0.117 | 0.255 |
| | 1 = straight | 1 = no bend |
| | 2 = bend | 2 = bend |

TABLE 6

Comparison of anther color of 'HB 129' and other Kentucky bluegrass varieties, year 2.

| Variety | Anther Color Categories (% of all anthers examined) Purple | Yellow | Brown |
|---|---|---|---|
| 'HB 129' | 100 | 0 | 0 |
| Adelphia | 67 | 33 | 0 |
| America | 46 | 54 | 0 |
| Baron | 16 | 84 | 0 |
| Julia | 26 | 74 | 0 |
| Langara | 65 | 35 | 0 |
| Midnight | 98 | 2 | 0 |
| Nugget | 70 | 30 | 0 |
| Moonshadow | 9 | 91 | 0 |
| Ram I | 100 | 0 | 0 |
| Touchdown | 11 | 89 | 0 |

TABLE 7

Leaf sheath morphological traits of Kentucky bluegrass accessions measured 2002-2003 from the PVP nursery and greenhouse measurements at the research facility of Pickseed West, Inc. Oregon.

| Bluegrass Accessions | Keel | Hairs on Surface | Hairs on Both Sides Under Collar |
|---|---|---|---|
| 'HB 129' | 2 | 1 | 1 = 8% 2 = 92% |
| America | 2 | 1 | 2 |
| Mercury | — | — | — |
| | 1 - absent<br>2 - present | 1 - absent<br>2 - present | 1 - absent<br>2 - present |

| Bluegrass Accessions | Base of Sheath Color | Surface Roughness To Touch |
|---|---|---|
| 'HB 129' | 1 | 1 |
| America | 1 | 1 |
| Mercury | — | — |
| | 1 - green<br>2 - red | 1 - smooth<br>2 - rough |

TABLE 8

Leaf blade morphological traits of Kentucky bluegrass accessions measured 2002-2003 from the PVP nursery and greenhouse measurements at the research facility of Pickseed West, Inc. Oregon.

| Bluegrass Accessions | Margin Hairs | Hairs Upper Side | Luster Lower Side |
|---|---|---|---|
| 'HB 129' | 2 | 2 = 82%<br>1 = 18% | 1 |
| America | 2 | 1 | 1 |
| Mercury | — | — | — |
| | 1 - absent<br>2 - present | 1 - absent<br>2 - sparse<br>3 - dense | 1 - shiny<br>2 - dull |

| Bluegrass Accessions | Luster Upper Side | Hairs on Lower Side | Blade Width |
|---|---|---|---|
| 'HB 129' | 2 | 1 | 5 |
| America | 2 | 1 | 2 |
| Mercury | — | — | — |
| | 1 - shiny<br>2 - dull | 1 - absent<br>2 - sparse<br>3 - dense | 1 - very fine<br>2 - fine<br>3 - medium<br>4 - broad<br>5 - very broad |

TABLE 9

Lemma morphological traits and seed phenol reaction of Kentucky bluegrass accessions measured 2002-2003 from the PVP nursery and greenhouse measurements at the research facility of Pickseed West, Inc. Oregon.

| Bluegrass Accessions | Lemma Keel | Marginal Nerves | Intermediate Nerves |
|---|---|---|---|
| 'HB 129' | 1 - 55%<br>2 - 45% | 1 - 30%<br>2 - 70% | 1 - 15%<br>2 - 85% |
| America | — | — | — |
| Mercury | 1 - 90%<br>2 - 10% | 2 | 2 |
| | 1 - glabrous<br>2 - slight pubescence<br>3 - pubescent | 1 - Yes<br>2 - No | 1 - distinct<br>2 - obscure |

| Bluegrass Accessions | Lemma Basal Webbing | Seed Phenol Reaction |
|---|---|---|
| 'HB 129' | 1 - 90%<br>2 - 10% | 1 - 10%<br>2 - 90% |
| America | — | — |
| Mercury | 2 | 1 - 5%<br>2 - 95% |
| | 1 - absent<br>2 - scant<br>3 - copious | 1 - none<br>2 - beige<br>3 - brown<br>4 - black after 4 hrs<br>5 - black after 24 hrs |

TABLE 10

Plant spread, hairs on ligule and leaf sheath glaucosity of Kentucky bluegrass accessions measured 2002-2003 from the PVP nursery and greenhouse measurements at the research facility of Pickseed West, Inc. Oregon.

| Bluegrass Accessions | Amount of Spread in 1 year via Rhizomes (cm) | Hairs on Ligule | Leaf Sheath Glaucosity |
|---|---|---|---|
| 'HB 129' | 64 | 1 - 53%<br>2 - 47% | 2 |
| America | — | — | — |
| Mercury | 49 | 1 | 1 - 17% 2 - 83% |
| | | 1 - absent<br>2 - short<br>3 - long | 1 - absent<br>2 - present |

The seed of 'HB 129' was conditioned by removing most of the extraneous materials that may have been harvested with the seed, such as small pieces of plant stems and leaves, soil particles, seed of other plants and the like. This conditioned seed of 'HB 129' averages 2.75 mm in length, and 0.97 mm in width. 'HB 129' has about 840,700 seeds per pound.

Comparisons of 'HB 129' with other Kentucky bluegrass varieties in terms of seed length, seed width and 1000 seed weight are shown in Table 11 as follows:

TABLE 11

Comparison of seed length, seed width and 1000 seed weight of 'HB 129' and other Kentucky bluegrass varieties and a hybrid for years 1 & 2.

| Variety | Seed length (mm) Year 1 | Seed Width (mm) Year 1 | 1000 seed weight (g) Year 1 | 1000 seed weight (g) Year 2 |
|---|---|---|---|---|
| 'HB 129' | 2.75 | 0.97 | 0.657 | 0.423 |
| Touchdown | 3.00 | 0.92 | 0.753 | 0.417 |
| Baron | 2.87 | 0.97 | 0.690 | 0.467 |
| Ram I | 3.20 | 0.91 | 0.647 | 0.437 |
| Midnight | 3.03 | 0.81 | 0.637 | 0.403 |
| Julia | 2.82 | 0.82 | 0.630 | 0.507 |
| Langara | 2.77 | 0.80 | 0.573 | 0.463 |
| Adelphia | 2.90 | 0.83 | 0.560 | 0.340 |
| Moonshadow | 2.57 | 0.87 | 0.553 | 0.330 |
| Nugget | 3.22 | 0.90 | 0.543 | 0.200 |
| America | 2.63 | 0.83 | 0.470 | 0.383 |
| LSD (0.05) | 0.4 | 0.067 | 0.09 | 0.074 |

'HB 129' has demonstrated relatively rapid germination and emergence compared to other hybrids including Reveille in both fall and spring sowings (Table 12). 'HB 129' has shown greatly reduced seed cotton compared to Reveille. It is thought that the presence of the cotton on seed has led to poor seed recovery, and the availability of Reveille predominantly as a vegetatively reproduced product from rhizome and tiller materials.

TABLE 12

Germination rating comparison for 'HB 129' to hybrid bluegrasses and Kentucky bluegrasses planted in turfgrass plots at Cleveland, Texas.

| Treatment | Plant type | Germination Rating: Seeded Nov. 11, 1999 15 days after seeding | Germination Rating: Seeded Feb. 28, 2000 8 days after seeding |
|---|---|---|---|
| 'HB 129' | Tx × Ky | 2.7 | 1.7 |
| Ascot | Ky | 2.7 | 2.7 |
| Abbey | Ky | 1.7 | 2.0 |
| Coventry | Ky | 1.7 | 1.3 |
| Reveille | Tx × Ky | 0.0 | 0.0 |
| LSD (0.05) | | 0.90 | 0.74 |

Tx × Ky - Texas × Kentucky bluegrass hybrid
Ky - Kentucky bluegrass
0 - no germinated seed visible
9 - all seed germinated and visible

TABLE 13

Comparison of 'HB 129' to other hybrid bluegrasses for cotton on seed.

| Treatment | Seed cotton rating 1 - no or little cotton, 2 - scant cotton, 3 - copious cotton |
|---|---|
| 'HB 129' | 1 |
| Reveille | 3 |

'HB 129' has performed well throughout the U.S. as exhibited by good turf quality ratings under reduced management inputs in comparison with other Kentucky bluegrass varieties and other Texas×Kentucky bluegrass hybrids. In addition, it has a light green color with good turf density which can be maintained throughout the growing season providing a rapid development of sod strength, and a medium to high seed yielding capacity.

TABLE 14

Comparison of 'HB 129' with Texas bluegrass and Kentucky bluegrasses.

| Variety | Plant Height (cm) | Longest Rhizome (cm) | Panicle Length (mm) | Flag Leaf Length (mm) | Flag Leaf Width (mm) | Flag Leaf Sheath Length (mm) |
|---|---|---|---|---|---|---|
| 'HB 129' | 41.5 | 49.0 | 25.6 | 25.6 | 4.0 | 74.3 |
| Unique | 17.3 | 40.0 | 34.7 | 14.2 | 1.2 | 48.5 |
| Abbey | 37.0 | 44.0 | 62.8 | 21.1 | 3.5 | 76.3 |
| Texas bluegrass | 80.0 | 53.3 | 126.9 | 97.2 | 6.4 | 146.9 |
| Midnight | 21.8 | 36.6 | — | — | — | — |
| Touchdown | 39.8 | 50.0 | 27.4 | 27.4 | 3.6 | 66.5 |
| Limousine | 29.8 | 40.8 | 18.9 | 18.9 | 3.2 | 52.5 |
| LSD (0.05) | 14.0 | 9.8 | 22.2 | 15.0 | 0.5 | 25.8 |

'HB 129' bluegrass has been shown to provide excellent fall establishment rate, winter density and good seedling vigor (Table 15). Spring establishment rate is similar to other bluegrasses. 'HB 129' bluegrass has been shown to possess a rapid development of sod strength as compared to other bluegrasses (Table 15, sod stretch). 'HB 129' bluegrass has been shown to compete well with Poa annua (Table 15). 'HB 129' bluegrass has been shown to produce a relatively high number of seedheads under mowing as compared to other bluegrasses.

TABLE 15

Differences between 'HB 129' and other Entries Detected in the 2001 and 2002 Progress Reports of the 2000 National Kentucky Bluegrass Evaluation Program for Kentucky Bluegrass.

| Genotype/Cultivar | Establishment Rating % | | Seedhead Rating | | Winter Density |
|---|---|---|---|---|---|
| | | UT | NJ Locations | | WA |
| | 12 | 1 | 1 | 5 | 1 |
| | Year | | | | |
| 'HB 129' | 2001 | 2001 | 2001 | 2002 | 2001 |
| 1B7-308 | o | | | | |
| 99AN-53 | o | | | o | |
| A96-427 | o | | | o | o |
| A96-451 | o | | o | o | |
| A96-739 | o | | | o | |
| A96-742 | | | | | |
| A97-1330 | | | o | o | |
| A97-1409 | o | | | o | |
| A97-1432 | o | | o | o | |
| A97-1715 | o | | | | o |
| A97-857 | o | | | | |
| A98-1028 | o | | | o | |
| A98-139 | o | | | | |
| A98-183 | o | | | | o |
| A98-365 | o | | | o | o |
| A98-407 | o | | o | o | o |
| A98-881 | o | | | | |
| Abbey | x | | | o | |
| Allure | o | x | o | o | |
| Alpine | | x | | | |
| Apollo | | | o | o | |
| Arcadia | | | | | |
| Arrow | | | o | o | |
| Ascot | o | | o | o | o |
| AVALANCHE | | | x | | |
| Award | | | x | | |

TABLE 15-continued

Differences between 'HB 129' and other Entries Detected in the 2001 and 2002 Progress Reports of the 2000 National Kentucky Bluegrass Evaluation Program for Kentucky Bluegrass.

| | | | | | |
|---|---|---|---|---|---|
| Awesome | | | x | | |
| B3-171 | o | | o | o | |
| B3-185 | o | | o | o | |
| B4-128A | o | | | | |
| B5-144 | o | | o | o | |
| B5-43 | o | | o | o | |
| B5-45 | o | | | o | |
| BAR Pp 0468 | o | | o | o | |
| BAR Pp 0471 | o | | o | o | |
| BAR Pp 0566 | o | | o | o | o |
| BAR Pp 0573 | o | | o | o | o |
| Bariris | | | | o | |
| Baritone | o | | | o | |
| Baron | o | | o | o | |
| Baronette | | | o | o | |
| Baronic | | | o | o | |
| Barrister | | x | | | o |
| Bartitia | | | o | o | |
| Barzan | o | | | o | |
| Bedazzled | | | o | o | |
| Beyond | | | | | |
| Blacksburg II | o | | | | |
| Blackstone | | | x | | |
| Blue Knight | o | | | o | |
| Blue Ridge | o | | o | o | |
| Bluemax | o | | o | | o |
| Bluestone | o | | x | | |
| Bodacious | o | | o | o | o |
| Boomerang | o | | | o | |
| Bordeaux | | | o | o | |
| Boutique | o | | | o | |
| Brilliant | | | o | o | |
| Brooklawn | o | | o | o | |
| Cabernet | o | | | | |
| Champagne | | | | | |
| Champlain | o | | | | |
| Chateau | o | | o | o | |
| Chelsea | o | | | o | |
| Chicago II | | | | | |
| Coventry | | | | o | |
| CVB-20631 | o | | o | o | o |
| DLF 76-9032 | o | | x | | o |
| DLF 76-9034 | o | o | | | |
| DLF 76-9036 | | | o | o | |
| DLF 76-9037 | | | o | o | |
| Eagleton | | x | | | |
| Envicta | | | o | o | |
| Everest | o | | x | | |
| EverGlade | o | | x | | o |
| Excursion | o | | | | |
| Fairfax | o | | | o | |
| Freedom II | | | | | |
| Ginney | | | x | | |
| Glenmont | | | | o | |
| GO-9LM9 | x | | x | | |
| Goldrush | | | o | o | |
| Goldstar | | x | | o | |
| H92-203 | | | o | o | |
| H92-558 | o | x | | o | |
| Hallmark | | | | | |
| HV 140 | | | o | o | |
| HV-238 | o | | | | |
| Impact | | | | | |
| J-1513 | | | x | | |
| J-1838 | o | | x | | |
| J-2561 | o | | x | | |
| J-2885 | o | | | | |
| J-2890 | | | x | | |
| Jefferson | | | | o | |
| Jewel | o | | x | | o |
| Julia | o | | | o | |
| Julius | o | | o | o | |
| Kenblue | x | | x | | |
| Lakeshore | | | | o | o |

TABLE 15-continued

Differences between 'HB 129' and other Entries Detected in the 2001 and 2002 Progress Reports of the 2000 National Kentucky Bluegrass Evaluation Program for Kentucky Bluegrass.

| | | | | | |
|---|---|---|---|---|---|
| Langara | | x | | | |
| Liberator | | | | | o |
| Lily | | | | o | |
| Limerick | | | o | o | |
| Limousine | | | | o | |
| Mallard | | | o | o | o |
| Markham | o | | | | |
| Marquis | | | o | o | |
| Mercury | | | o | o | |
| Midnight | o | | | | |
| Midnight II | | | x | o | |
| Misty | | | o | o | |
| Monte Carlo | o | | o | o | |
| Moon Shadow | o | | | | |
| Moonlight | | | | | |
| NA-K992 | o | | o | o | |
| North Star | o | | o | o | o |
| NuDensity | | | x | | |
| NuGlade | | | x | | |
| Odyssey | | | x | | |
| Perfection | | | | | |
| Pick 417 | o | | | | |
| Pick 453 | o | | | | |
| Pp H 6366 | | | | o | |
| Pp H 6370 | | | o | | |
| Pp H 7832 | o | | | o | |
| Pp H 7907 | o | | o | o | o |
| Pp H 7929 | o | | o | o | o |
| Princeton 105 | o | | | o | |
| Pro Seeds - 453 | o | | | | |
| PST-108-79 | o | | | o | |
| PST-161 | o | | | | |
| PST-1804 | | | | | |
| PST-222 | o | | o | o | |
| PST-604 | o | | | o | |
| PST-B3-170 | o | | o | o | |
| PST-B4-246 | o | | | o | |
| PST-B5-125 | o | | | | o |
| PST-H5-35 | o | | | | |
| PST-H6-150 | o | | o | | o |
| PST-York Harbor 4 | | | | o | |
| Quantum Leap | o | | | | |
| Rambo | | | o | | |
| Raven | | | o | o | |
| Rita | o | | | o | |
| Royale | o | | | o | o |
| Royce | | | o | o | |
| Rugby II | | | | o | |
| Serene | | | | | |
| Shamrock | | | | | |
| Showcase | o | | o | o | |
| SI A96-386 | o | | | o | o |
| Sonoma | | | o | | |
| SR 2284 | | | | o | |
| SRX 2114 | o | | | o | |
| SRX 2394 | | | | o | |
| SRX 26351 | | | | o | |
| SRX 27921 | o | | | o | |
| SRX QG245 | o | | | o | |
| Total Eclipse | o | | | | |
| Tsunami | | | x | | |
| Unique | | | o | | |
| Unknown | | | x | o | |
| Voyager II | o | | o | | |
| Washington | x | | x | o | |
| Wellington | | | x | | |
| Wildwood | x | | | | |

TABLE 15-continued

Differences between 'HB 129' and other Entries Detected in the 2001 and 2002 Progress Reports of the 2000 National Kentucky Bluegrass Evaluation Program for Kentucky Bluegrass.

| | *Poa annua* % | | Sod Stretching | | |
|---|---|---|---|---|---|
| | May | Nov. | Lbs. | | Seeding |
| | NJ | NJ | NE | NE | Vigor |
| | | | Locations | | |
| | 1 | 1 | 1 | 1 | 18 |
| Genotype/Cultivar | | | Year | | |
| 'HB 129' | 2002 | 2002 | 2001 | 2002 | 2001 |
| 1B7-308 | o | | o | | o |
| 99AN-53 | o | | o | | o |
| A96-427 | o | | o | | o |
| A96-451 | o | | | | o |
| A96-739 | o | | o | | o |
| A96-742 | o | x | o | | |
| A97-1330 | o | x | o | | |
| A97-1409 | o | | o | | o |
| A97-1432 | o | x | o | | o |
| A97-1715 | o | | x | | o |
| A97-857 | o | | o | | o |
| A98-1028 | o | | | o | o |
| A98-139 | o | x | o | | |
| A98-183 | o | x | o | o | o |
| A98-365 | o | x | o | | o |
| A98-407 | o | | o | | o |
| A98-881 | o | | o | o | |
| Abbey | o | | o | | x |
| Allure | | | o | | o |
| Alpine | | | o | | |
| Apollo | o | x | o | | |
| Arcadia | o | | | | |
| Arrow | o | | o | | |
| Ascot | o | | o | | o |
| AVALANCHE | | | o | | |
| Award | | o | o | | |
| Awesome | o | | o | | |
| B3-171 | o | x | o | o | o |
| B3-185 | o | x | | | o |
| B4-128A | o | | o | | o |
| B5-144 | | | o | | o |
| B5-43 | | | o | o | o |
| B5-45 | o | x | o | o | o |
| BAR Pp 0468 | o | x | o | | o |
| BAR Pp 0471 | o | x | o | | o |
| BAR Pp 0566 | o | | o | | o |
| BAR Pp 0573 | o | x | o | | o |
| Bariris | o | | o | | |
| Baritone | o | | o | o | o |
| Baron | o | x | o | | |
| Baronette | o | | o | | |
| Baronic | o | | o | | |
| Barrister | o | o | o | | |
| Bartitia | o | | o | | |
| Barzan | | | o | o | o |
| Bedazzled | | | | o | |
| Beyond | | | o | | |
| Blacksburg II | o | | | o | o |
| Blackstone | | o | x | | |
| Blue Knight | o | | | | |
| Blue Ridge | o | | o | | o |
| Bluemax | o | | o | | o |
| Bluestone | o | | | | o |
| Bodacious | o | x | o | | o |
| Boomerang | o | | o | | o |
| Bordeaux | o | | o | | |
| Boutique | o | | o | | o |
| Brilliant | o | x | o | o | |
| Brooklawn | | | | | o |
| Cabernet | | | o | | o |
| Champagne | o | | | | |

TABLE 15-continued

Differences between 'HB 129' and other Entries Detected in the 2001 and 2002 Progress Reports of the 2000 National Kentucky Bluegrass Evaluation Program for Kentucky Bluegrass.

| | | | | | |
|---|---|---|---|---|---|
| Champlain | | | o | | o |
| Chateau | | | o | o | o |
| Chelsea | o | | o | o | o |
| Chicago II | o | | o | | |
| Coventry | | | | o | |
| CVB-20631 | o | x | o | o | o |
| DLF 76-9032 | o | x | o | | o |
| DLF 76-9034 | o | | o | o | o |
| DLF 76-9036 | | | o | | |
| DLF 76-9037 | o | x | | | |
| Eagleton | | | o | | |
| Envicta | | | o | | |
| Everest | o | | | | o |
| EverGlade | o | | o | o | o |
| Excursion | o | | o | | |
| Fairfax | | | o | | |
| Freedom II | o | | o | | o |
| Ginney | o | | | | |
| Glenmont | o | x | o | | |
| GO-9LM9 | o | | o | o | x |
| Goldrush | o | | | | |
| Goldstar | o | x | o | o | |
| H92-203 | o | x | o | | o |
| H92-558 | o | | o | | o |
| Hallmark | | | o | | |
| HV 140 | o | x | o | o | |
| HV-238 | | | o | | o |
| Impact | o | | o | | |
| J-1513 | o | | o | | |
| J-1838 | o | | o | | o |
| J-2561 | o | | o | o | o |
| J-2885 | o | | o | | o |
| J-2890 | o | | o | | |
| Jefferson | | | o | | |
| Jewel | o | | o | | |
| Julia | o | | o | | o |
| Julius | | | o | o | o |
| Kenblue | | | o | | x |
| Lakeshore | o | | o | | o |
| Langara | | | o | | |
| Liberator | o | | x | o | |
| Lily | | | o | o | |
| Limerick | o | | o | | |
| Limousine | | | | | |
| Mallard | o | | | | |
| Markham | o | | o | | o |
| Marquis | | | o | | o |
| Mercury | o | x | o | o | |
| Midnight | o | | x | | o |
| Midnight II | | o | o | | |
| Misty | | | o | | |
| Monte Carlo | o | | o | | o |
| Moon Shadow | o | | o | | o |
| Moonlight | | | o | | |
| NA-K992 | o | | o | o | o |
| North Star | | | | | o |
| NuDensity | o | | o | | |
| NuGlade | o | | | | |
| Odyssey | o | | o | | |
| Perfection | o | | o | | |
| Pick 417 | | | o | | o |
| Pick 453 | o | | | | o |
| Pp H 6366 | o | | o | | |
| Pp H 6370 | | | | | |
| Pp H 7832 | | | o | | o |
| Pp H 7907 | | | o | o | o |
| Pp H 7929 | o | | o | | o |
| Princeton 105 | o | | o | | |
| Pro Seeds - 453 | | o | | | o |
| PST-108-79 | | | o | | o |
| PST-161 | o | | o | | o |
| PST-1804 | | | o | | |
| PST-222 | o | | | o | o |
| PST-604 | o | | o | | o |

TABLE 15-continued

Differences between 'HB 129' and other Entries Detected in the 2001 and 2002 Progress Reports of the 2000 National Kentucky Bluegrass Evaluation Program for Kentucky Bluegrass.

| | | | | | |
|---|---|---|---|---|---|
| PST-B3-170 | o | x | o | o | o |
| PST-B4-246 | o | | o | | o |
| PST-B5-125 | o | | o | | o |
| PST-H5-35 | o | | o | o | o |
| PST-H6-150 | o | | o | | o |
| PST-York Harbor 4 | o | x | o | | o |
| Quantum Leap | o | | o | o | o |
| Rambo | o | | o | | |
| Raven | o | | o | | |
| Rita | | | o | | o |
| Royale | o | | o | o | o |
| Royce | o | | o | | |
| Rugby II | o | x | o | | o |
| Serene | o | | o | | |
| Shamrock | | | o | | |
| Showcase | o | | o | | o |
| SI A96-386 | o | x | o | | o |
| Sonoma | o | | o | o | o |
| SR 2284 | o | | o | | o |
| SRX 2114 | | | o | | |
| SRX 2394 | | | o | o | |
| SRX 26351 | o | | o | | |
| SRX 27921 | o | | o | | o |
| SRX QG245 | o | | o | | |
| Total Eclipse | o | | o | | |
| Tsunami | o | | o | | |
| Unique | o | | o | | o |
| Unknown | o | x | o | | |
| Voyager II | o | | o | | o |
| Washington | o | x | o | | x |
| Wellington | | | o | | |
| Wildwood | o | | o | o | |

o Denotes significantly lesser or poorer performance than 'HB 129' ('HB 129') based on LSD Values
x Denotes significantly greater or better performance than 'HB 129' ('HB 129') based on LSD Values
Denotes similar or comparable performance to 'HB 129' ('HB 129') based on LSD Values With regard to a comparative analysis conducted for purposes of determining color of 'HB 129' plants relative to Kentucky bluegrass varieties and a hybrid bluegrass, readings were taken of the vegetative color of 'HB 129' on actively growing plants with adequate nutrient and water availability. Color readings showed that 'HB 129' leaves had a light green color without blue-green. This was dissimilar to the Kentucky bluegrasses with the exception of Touchdown (Table 16).

TABLE 16

Comparison of ratings for growth habit, leaf color and leaf blade width for 'HB 129' and other Kentucky bluegrass varieties, year 2.

| Variety | Growth Habit | Leaf Color Green |
|---|---|---|
| 'HB 129' | 2.0 | 1.0 |
| Langara | 3.0 | 3.1 |
| Julia | 2.1 | 1.6 |
| Adelphia | 2.0 | 2.4 |
| Touchdown | 1.9 | 1.0 |
| America | 1.9 | 2.8 |
| Midnight | 1.3 | 3.1 |
| Baron | 1.3 | 1.2 |
| Ram I | 1.2 | 2.0 |
| Nugget | 1.1 | 2.5 |
| LSD (0.05) | 0.4201 | 0.3899 |
| | 1 - Prostrate | 1 - Light Green |

TABLE 16-continued

Comparison of ratings for growth habit, leaf color and leaf blade width for 'HB 129' and other Kentucky bluegrass varieties, year 2.

| | | |
|---|---|---|
| | 2 - Semi-Prostrate | 2 - Medium Green |
| | 3 - Erect | 3 - Mod Dark Green |
| | | 4 - Very Dark Green |
| Variety | Leaf Color Blue Green | Blade Width |
| 'HB 129' | 1.0 | 4.5 |
| Langara | 1.9 | 3.6 |
| Julia | 1.4 | 3.2 |
| Adelphia | 1.8 | 4.0 |
| Touchdown | 1.0 | 4.9 |
| America | 2.3 | 3.1 |
| Midnight | 1.5 | 2.7 |
| Baron | 1.4 | 4.8 |
| Ram I | 1.0 | 3.9 |
| Nugget | 1.7 | 2.8 |
| LSD (0.05) | 0.5288 | 0.5025 |
| | 1 - Not Blue Green | 1 - Very Fine |
| | 2 - Mod Blue Green | 2 - Fine |
| | 3 - Blue-Green | 3 - Medium |
| | 4 - Strong Blue-Green | 4 - Broad |
| | | 5 - Very Broad |

Further comparative testing of 'HB 129' plants relative to Kentucky bluegrass, Texas bluegrass and hybrid varieties was conducted and the results of this testing are set forth in the following Table 17 and Table 18:

TABLE 17

Comparison of morphological traits of flowering tillers of plants allowed to over winter in the field and brought into a controlled greenhouse environment (60-75° F.) in late winter and allowed to grow undisturbed during the winter of 2004-2005 at The Scotts Company facility at Gervais, Oregon.

| Variety | Flag Leaf Ligule Length mm | Flag Leaf Ligule Hairs 0 = none 9 = Many | Flag Leaf Thickness (mm) | Anthesis (days to flowering) |
|---|---|---|---|---|
| 'HB 129' | 1.3 | 5.8 | 0.0149 | 138 |
| Reveille | 2.3 | 0.9 | 0.0207 | 141 |
| Geronimo | 1.7 | 7.1 | 0.0164 | 140 |
| Ascot | 2.0 | 5.6 | 0.0166 | 141 |
| Midnight | 0.8 | 3.9 | 0.0145 | 148 |
| Buckingham | 2.4 | 8.1 | 0.0190 | 142 |
| Texas Bluegrass (TX 51-90) | 1.7 | 0.1 | 0.0262 | 140 |
| Texas Bluegrass (TX 39-88) | 2.7 | 0.1 | 0.0199 | |
| Texas Bluegrass (TX 49-90) | 2.0 | 0.5 | 0.0231 | 140 |
| Kelly | 2.1 | 6.3 | 0.0163 | 143 |
| LSD (P = .05) | 0.663 | 1.93 | 0.003324 | 4.854 |

As shown in the tabulated results (Table 17), 'HB 129' has a shorter flag leaf ligule, more hairs on the flag leaf ligule and has a thinner flag leaf than Reveille hybrid Kentucky bluegrass and Texas bluegrass.

TABLE 18

Comparison of morphological traits of plant infloresence - spikelets, florets, glumes - from panicles harvested from a field nursery in 2005 at The Scotts Company facility at Gervais, Oregon.

| Variety | Spikelet Length 1stWhorl (mm) | Spikelet Length 3rdWhorl (mm) | Spikelet Width 1stWhorl (mm) | Spikelet Width 3rdWhorl (mm) |
|---|---|---|---|---|
| 'HB 129' | 7.6 | 7.1 | 4.5 | 4.0 |
| Reveille | 6.1 | 6.4 | 4.0 | 4.2 |
| Geronimo | 5.5 | 6.3 | 4.2 | 4.0 |
| Ascot | 5.6 | 5.8 | 4.4 | 4.3 |
| Midnight | 5.7 | 6.4 | 2.7 | 3.2 |
| Buckingham | 6.9 | 6.9 | 4.6 | 4.7 |
| Texas Bluegrass TX 51-90 | 7.6 | 7.5 | 7.3 | 7.1 |
| Texas Bluegrass TX 39-88 | 8.6 | 8.5 | 5.9 | 5.7 |
| Texas Bluegrass TX 49-90 | 9.7 | 9.7 | 8.2 | 8.0 |
| Kelly | 6.3 | 6.1 | 4.4 | 4.3 |
| LSD (P = .05) | 1.679 | 1.738 | 1.875 | 1.621 |

| Variety | Florets/ Spikelet 1stWhorl (Count) | Florets/ Spikelet 3rdWhorl (Count) | Lower Glume Length 1stWhorl (mm) | Lower Glume Length 3rdWhorl (mm) |
|---|---|---|---|---|
| 'HB 129' | 8.6 | 7.0 | 3.1 | 3.2 |
| Reveille | 4.0 | 4.9 | 2.9 | 3.3 |
| Geronimo | 5.2 | 6.0 | 2.7 | 3.0 |
| Ascot | 3.8 | 4.3 | 2.9 | 2.9 |
| Midnight | 4.3 | 5.8 | 2.7 | 2.6 |
| Buckingham | 6.7 | 7.1 | 3.1 | 3.0 |
| Texas Bluegrass TX 51-90 | 8.8 | 8.5 | 3.6 | 3.3 |
| Texas Bluegrass TX 39-88 | 8.0 | 7.9 | 3.6 | 3.6 |
| Texas Bluegrass TX 49-90 | 8.7 | 8.6 | 5.4 | 5.0 |
| Kelly | 4.3 | 4.9 | 2.8 | 2.9 |
| LSD (P = .05) | 1.69 | 1.81 | 0.853 | 0.682 |

TABLE 18-continued

Comparison of morphological traits of plant infloresence - spikelets, florets, glumes - from panicles harvested from a field nursery in 2005 at The Scotts Company facility at Gervais, Oregon.

| Variety | Upper Glume Length 1stWhorl (mm) | Upper Glume Length 3rdWhorl (mm) | Plant Height (cm) |
|---|---|---|---|
| 'HB 129' | 3.5 | 3.3 | 58.3 |
| Reveille | 3.3 | 3.5 | 51.6 |
| Geronimo | 2.9 | 3.1 | 56.9 |
| Ascot | 3.1 | 3.1 | 38.2 |
| Midnight | 3.1 | 3.2 | 29.7 |
| Buckingham | 3.4 | 3.4 | 48.2 |
| Texas Bluegrass TX 51-90 | 4.2 | 4.2 | 48.1 |
| Texas Bluegrass TX 39-88 | 4.0 | 4.2 | 60.4 |
| Texas Bluegrass TX 49-90 | 6.0 | 5.4 | 56.2 |
| Kelly | 3.0 | 3.0 | 38.0 |
| LSD (P = .05) | 0.951 | 0.803 | 8.807 |

As shown in the tabulated results (Table 18), the spikelet length in both the 1$^{st}$ and 3$^{rd}$ whorl of the panicle branch 'HB 129' is less than in Texas bluegrass but greater than Reveille, Geronimo, Ascot and Midnight.

What is claimed is:

1. A new and distinct hybrid variety of Texas bluegrass× Kentucky bluegrass plant, as herein illustrated and described and characterized by rapid establishment; a light green, dense turf; a wide leaf blade; aggressive rhizome growth; a reduced level of cotton on the seed; and a medium to high seed yield potential.

* * * * *